(12) United States Patent
Mann et al.

(10) Patent No.: US 9,891,194 B2
(45) Date of Patent: Feb. 13, 2018

(54) ACQUISITION OF FRAGMENT ION MASS SPECTRA OF IONS SEPARATED BY THEIR MOBILITY

(71) Applicants: Matthias Mann, Stockdorf (DE); Oliver Räther, Lilienthal (DE); Melvin Andrew Park, Billerica, MA (US); Markus Lubeck, Bremen (DE)

(72) Inventors: Matthias Mann, Stockdorf (DE); Oliver Räther, Lilienthal (DE); Melvin Andrew Park, Billerica, MA (US); Markus Lubeck, Bremen (DE)

(73) Assignees: Bruker Daltonik GmbH, Bremen (DE); Matthias Mann, Stockdorf (DE)

( * ) Notice: Subject to any disclaimer, the term of this patent is extended or adjusted under 35 U.S.C. 154(b) by 0 days.

(21) Appl. No.: 14/931,163

(22) Filed: Nov. 3, 2015

(65) Prior Publication Data

US 2017/0122906 A1 May 4, 2017

(51) Int. Cl.
*H01J 49/42* (2006.01)
*G01N 27/62* (2006.01)
*H01J 49/00* (2006.01)
*G01N 33/483* (2006.01)

(52) U.S. Cl.
CPC ......... *G01N 27/622* (2013.01); *G01N 33/483* (2013.01); *H01J 49/0031* (2013.01); *H01J 49/4215* (2013.01)

(58) Field of Classification Search
USPC ....................................................... 250/282
See application file for complete search history.

(56) References Cited

U.S. PATENT DOCUMENTS

| | | | | |
|---|---|---|---|---|
| 6,960,761 B2 * | 11/2005 | Clemmer | ............. | G01N 27/622 250/287 |
| 6,992,283 B2 * | 1/2006 | Bateman | ............. | G01N 27/622 250/281 |
| 7,838,826 B1 * | 11/2010 | Park | ..................... | G01N 27/622 250/281 |
| 8,288,717 B2 * | 10/2012 | Park | ..................... | G01N 27/622 250/281 |
| 8,766,176 B2 * | 7/2014 | Park | ..................... | G01N 27/626 250/281 |
| 9,164,060 B2 * | 10/2015 | Campbell | ........... | H01J 49/0031 |

FOREIGN PATENT DOCUMENTS

WO     2013140132 A2    9/2013

* cited by examiner

*Primary Examiner* — Phillip A Johnston
(74) *Attorney, Agent, or Firm* — Benoît & Côté Inc.

(57) ABSTRACT

The invention provides a method for acquiring fragment ion spectra of substances in complex substance mixtures wherein a trapped ion mobility spectrometer ("TIMS") is used as the ion mobility separator separation device. The fragment ion spectra may be used for the identification of high numbers of proteins in complex mixtures, or for a safe quantification of some substances, by their fragment ion mass spectra in a mass spectrometer with up-front substance separator. TIMS with parallel accumulation provides the unique possibility to prolong the ion accumulation duration to find more detectable ion species without decreasing the measuring capacity for fragment ion mass spectra. The high measurement capacity for fragment ion mass spectra permits the repeated measurement of low abundance ion species to improve the quality of the fragment ion spectra.

23 Claims, 5 Drawing Sheets

ACQUISITION OF FRAGMENT ION MASS SPECTRA OF IONS SEPARATED BY THEIR MOBILITY

BACKGROUND OF THE INVENTION

Field of the Invention

The invention relates to methods for the highly efficient acquisition of fragment ion mass spectra of precursor ions separated by their mobility in order to identify as many substances as possible in complex substance mixtures, in particular digest peptides in a bottom-up proteomics workflow, or to quantify substances with accurate identity.

Description of the Related Art

In protein science, there is an increasing interest in the identification of as many peptides and proteins as possible in liquid-chromatography/mass-spectrometry runs (LC-MS) of a proteolytic digest of proteins extracted from a biological sample. Mobility spectrometry, coupled to mass spectrometry, has been shown to improve the measurements to reach this goal. As an example for an instrument to perform these measurements, a combination apparatus with an up-front substance separator, e.g. a liquid chromatograph (LC), and a mass spectrometer (MS) may be used, the mass spectrometer equipped with an ion accumulator, an ion mobility separator, a mass filter (usually an RF quadrupole mass filter), an ion fragmentation cell, and downstream a high-resolution time-of-flight mass analyzer with orthogonal ion injection. FIG. 1 gives an example of such a typical instrument. An ion trap may be used to accumulate ions upstream of the ion mobility separator, and a drift tube ion mobility spectrometer to separate the ions by their mobility.

Using this instrument, a mass-mobility map as presented in FIG. 2 is measured, using the mobility separator and the time-of-flight analyzer without filtering masses and fragmenting Ions. The map usually shows the ion masses versus drift time in the drift tube. From this map, an ion species of interest with a specific mobility and mass is selected, indicated by the ellipse in FIG. 2. In a second cycle, fresh ions from the ion accumulator are again separated in time by their ion mobility. The mass filter is adjusted to select the ion species of interest during the specific drift time interval of the ion species, which are then fragmented in the fragmentation cell, and the desired fragment ion spectrum is acquired by the time-of-flight mass analyzer.

In document U.S. Pat. No. 6,960,761 B2 ("INSTRUMENT FOR SEPARATING IONS IN TIME AS FUNCTIONS OF PRESELECTED ION MOBILITY AND ION MASS", D. E. Clemmer, 2001), this simple data-dependent acquisition method of fragment ions is greatly improved with respect to a better utilization of ions from the ion source. This document describes a large variety of methods to separate ions in mixtures using a number of different combinations of ion sources, ion traps, ion mobility separators, mass filters, collision cells, ion reactors, and high resolution mass analyzers. Furthermore, correspondent apparatuses are described being combined in varying sequence from ion sources, ion traps, ion mobility separators, mass filters, collision cells, ion reactors, and high resolution mass analyzers. Ion traps are used to accumulate ions. Drift tube ion mobility spectrometers with moderate length are applied as ion mobility separators. Among the variations of apparatuses, a device according to FIG. 1 (see Clemmer, FIG. 9 and claims 21 and 22), and an operation method as shown in FIG. 4 can be found (see Clemmer, FIG. 13 and claims 4 and 5). The method with sequential measurements of selected ion species is described in the text (see Clemmer, column 20, line 64 to column 21, line 21). FIG. 3 shows an artificially constructed mass-mobility map of a first measurement cycle. Several (about five following the figures given by Clemmer) ion species of interest are selected in the mass-mobility map. The selected ion species must be sufficiently separated in time by their different mobilities. The time between the selected ion species has to be chosen such that the voltages of the quadrupole mass filter can be switched electronically to filter the selected ion species to be measured next. In a subsequent measurement cycle, fresh ions are accumulated in the ion trap and then separated according to their ion mobility (this part of the method is not clearly outlined by Clemmer and can only be indirectly derived from FIG. 13). If the ion species of interest are not clearly separated by their ion mobilities without any overlap, the ion species are selected in drift time and mass, one after the other, by the mass filter, fragmented in the fragmentation cell, and measured as fragment ion mass spectra by the time-of-flight analyzer. From Clemmer's FIGS. 14 and 15 it can be concluded that about five fragment ion mass spectra can be obtained in a single measuring cycle. In a next cycle, the fragment ion spectra of other ion species selected from the same mass-mobility map may be measured, and so on. In this way, the utilization of ions from the ion source is greatly improved because different ion species being present in a LC peak are separated from each other in time and therefore enriched in their corresponding mobility peaks which are temporally shorter than the LC peak such that more than a hundred fragment ion spectra may be measured in a single second, provided that number of different ion species can be detected in the mass-mobility map. This may not be always the case.

The flow diagram of the essential part of this multi-cycle procedure is outlined in FIG. 4. The diagram describes one of the methods invented by D. E. Clemmer more than a dozen years ago, but introduces new terms "measurement loop" and "measurement cycle" for the sake of clarity.

In document WO 2013/140132 A2 ("MULTI-DIMENSIONAL SURVEY SCANS FOR IMPROVED DATA DEPENDENT ACQUISITIONS" K. Giles and J. L. Wildgoose, 2013), the method is generalized to separations by two different ion characteristics, for example mass and mobility.

At present, there are two commercial instruments on the market which correspond to the type presented in FIG. 1. The Agilent 6560 Ion Mobility Quadrupole Time-of-Flight LC/MS system features a trapping funnel for ion accumulation and an eighty-centimeter drift tube ($R_{mob} \approx 60$) for mobility scans with about fifty milliseconds drift duration for the complete range of mobilities. The Waters Vion IMS QToF mass spectrometer uses a traveling wave ion mobility spectrometer ($R_{mob} \approx 30$) to separate ions by their ion mobility. In both instruments, a prolongation of the scan duration, e.g. by lowering the drift field voltage, decreases the ion mobility resolution. The highest ion mobility resolution will be reached with the highest ion mobility scan speed and thus the lowest ion mobility scan duration, however, there are practical limits to obey. Essentially, there is scarcely any possibility to adapt the separation characteristics to the requirements of the analytical task.

The trapped ion mobility spectrometer ("TIMS") is an ion mobility spectrometer quite different from both drift tubes at constant electric field (in short: drift tubes) and travelling wave mobility spectrometers. An electric field barrier in a gas flow is used to hold back ions by their ion mobility; a decrease of the field barrier releases ions with increasing ion mobility, resulting in an ion mobility spectrum. The extraordinary and unique characteristic of TIMS is the fact that the ion mobility resolution continually increases with increasing scan duration. The TIMS is described in detail in document U.S. Pat. No. 7,838,826 B1 (M. A. Park, 2008).

There is a need to improve methods for the acquisition of high numbers of fragment ion mass spectra from proteolytic digests of proteins extracted from a biological sample, especially with the goal of finding and identifying as many ion species as possible in the mass-mobility map. Highest detectability for the ion species generated in the ion source of a mass spectrometer requires the collection of as many ions as possible. The collection of more ions, however, should not decrease the number of possible measurements of fragment ion mass spectra per unit of time. Furthermore, there is a need for improved methods to quantify substances in proteolytic digests of proteins extracted from a biological sample.

SUMMARY OF THE INVENTION

The invention provides a multi-cycle method to acquire fragment ion spectra of substances in complex substance mixtures by a mass spectrometer with an ion source, an ion mobility separator, a mass filter, an ion fragmentation cell, and a mass analyzer. In a first measurement cycle, a map with ion mobility scan times versus ion masses is measured, from which several sets of temporally separated ion species with distinct masses and distinct mobility scan times can be selected. In further measurement cycles, the ion species of a set each are selected by their mobility scan time, filtered by mass in the mass filter, and fragmented in the fragmentation cell, and the fragment ion mass spectra are measured by the mass analyzer. The method is characterized by the fact that a trapped ion mobility spectrometer (TIMS) is used as ion mobility separator.

TIMS replaces the drift tube ion mobility separator used by D. E. Clemmer. As usual, the mass spectrometer may be optionally equipped with an up-front substance separator, such as a liquid chromatograph or a capillary electrophoresis unit. Such an instrument is depicted in FIG. 5. The introduction and use of TIMS instead of a classical mobility spectrometer is not just a simple replacement: different modes of operation offer several unique advantages, some of which become only visible by a deep study of the characteristics of TIMS.

TIMS achieves a mobility resolution of 60 at scan durations of 20 milliseconds. In the average, about 2.5 milliseconds will be needed for the full acquisition of a fragment ion mass spectrum, including switching the mass filter to the next mass, filtering the selected ion species, fragmenting the ions of this ion species, and measuring the fragment ion mass spectrum by the mass analyzer (usually a time-of-flight mass analyzer). In general, the width of the ion mobility peak amounts to about one to two milliseconds. Within these 20 milliseconds ion mobility scan duration, the fragment ion mass spectra of a set of eight selected ion species can be measured. Considering some ion transfer times between the measurement cycles, a set of eight ion species in only 20 milliseconds permits the acquisition of more than 300 fragment ion mass spectra per second.

In a first embodiment, the TIMS is operated in parallel accumulation mode in which ions are provided from the ion source to the ion mobility separator during a measurement cycle and accumulated parallel to the measurement cycles. The ion accumulation durations can be adapted to obtain a predetermined number of detectable ion species in the map. Preferably, the ion mobility scan duration of the TIMS is substantially equal to the ion accumulation duration. TIMS with parallel ion accumulation is described in U.S. patent application Ser. No. 14/614,456 ("Trapping Ion Mobility Spectrometer with Parallel Accumulation", M. A. Park and M. Schubert).

TIMS with parallel accumulation provides the unique possibility to prolong the ion accumulation duration to find more detectable ion species without decreasing the measuring capacity for fragment ion mass spectra. Preferably, the ions are collected in the accumulator unit at a rising edge of an electric field barrier such that they get spatially separated by their ion mobility along the rising edge. Therefore, the accumulated ions are less influenced by space charge than in the accumulators used in the drift tube or traveling wave ion mobility separators. Of greatest importance, however, is the unique feature of TIMS that the longer accumulation period permits to increase the mobility resolution by choosing correspondingly longer mobility scan durations, e.g. 100 milliseconds scan duration with an ion mobility resolution of $R_{mob}=90$. As a consequence of the higher number of ions collected and the better ion mobility resolution, more ion species can be detected in the mass-mobility map. The acquisition rate of fragment ion spectra thereby remains essentially constant because the temporal width of the separated mobility peaks is still in the same order of magnitude as the typical time needed for acquiring a fragment ion spectrum (2.5 milliseconds or less).

In a second embodiment, TIMS is operated in the parallel accumulation mode further using a spatial or temporal zoom. In spatial zoom mode, ions are again accumulated in the accumulator unit at a rising edge of an electric field barrier. However, the rising edge of the electric field barrier used for the spatial zoom is made flatter and comprises a field peak at the end of the rising edge which keeps back ions species of low mobility during ion accumulation. Ion species of a selected mobility range are accumulated on a part of the rising edge having a much smaller field gradient compared to the field peak. The selected ion species are spatially decompressed compared to the ion species to reduce the effects of space charge, allowing for the undisturbed collection of many more ion species in the selected ion mobility range using longer accumulation duration. The electric field barrier of the spatial zoom may further comprise a steep electric field gradient at the beginning of the electric field barrier. The mobility-mass map of the selected ion species is then measured with a limited mobility range. The spatial zoom allows for the undisturbed detection and collection of still higher numbers of ions in selected ion mobility ranges during longer accumulation periods. At the same time, the ion mobility resolution furthermore increases, because a smaller range of mobilities is scanned. The method makes ions detectable which cannot be seen in any operation mode of any other commercial mass spectrometer with ion mobility separator. The selected ion mobility ranges of the spatial zoom can be adapted to the ion mobility distribution of the ion species generated from the substance mixture.

An LC-MS instrument typically does not deliver 300 different ion species which are detectable in a mass-mobility map measured with accumulation durations of 20 milliseconds. The capacity of the instrument to measure more than 300 fragment ion mass spectra per second cannot be fully exploited in this mode of operation.

One of the main problems with the data-dependent state-of-the-art methods is the detectability of ion species in the mass-mobility map. If an ion species cannot be detected in the mass-mobility map, no fragment ion spectrum can be obtained in a data-dependent acquisition of fragment ion spectra. Higher detectability requires higher numbers of ions to be accumulated. For an optimized ion source, higher numbers of ions can only be obtained by enlarging the accumulation duration. For drift tube or traveling wave ion mobility separators, longer accumulation durations in up-front ion traps or the like reduce proportionally the acquisition rate of fragment ion spectra because during the longer accumulation in ion traps, only one measurement cycle for measurements of fragment ion mass spectra can be performed. Besides, the accumulation time cannot be enlarged too much because only a limited amount of ions can be inserted into the drift tube without severe space charge effects.

The methods according to the invention can further comprise the measurement of additional mass-mobility maps. A new mass-mobility map is preferably measured when a predetermined time interval is over, when a predetermined number of fragment ion spectra are acquired or when the present mass-mobility map essentially no longer offers sufficient unmeasured ion species to be selected. The ion accumulation duration of a new mass-mobility map can differ from the ion accumulation duration of the preceding mass-mobility map, e.g. the ion accumulation duration can be increased in order to obtain more detectable ion species in the subsequent mass-mobility map. Furthermore, the mobility ranges of the measured mass-mobility maps can differ from each other. The selected mobility ranges can be adjusted in successively measured mass-mobility maps to cover all ion species of interest in the sample.

The methods according to the invention can further comprise repeated measurements of fragment ion mass spectra of the same ion species in subsequent measurement cycles to improve their quality. The repetitive measurements of fragment ion mass spectra of the same ion species is ended when a predefined quality is obtained or when the ion species is identified in a database search using the fragment ion spectra.

The complex substance mixture is typically a proteolytic digest of proteins extracted from a biological sample. The digest peptides are preferably separated by an up-front liquid chromatograph or electrophoresis unit. The fragment ion spectra of the digest peptides ions are used to identify the corresponding proteins by a database search as commonly known in the bottom-up proteomics workflow.

Another method according to the invention concerns accurate quantitation of substances in mixtures. Repeated measurements with short ion mobility scan durations and high numbers of measurement cycles per second are particularly suited to accurately quantify selected proteins or peptides with high precision. For example, especially tagged peptide ions separate "reporter ions" in the collision cell which may be measured in each measurement cycle covering a complete LC peak to improve the quantitation. This method may not need a high detectability to get high numbers of ion species, the selection of a few precursor ions may suffice the analytical requirements.

The mass analyzer is preferably a time-of-flight analyzer with orthogonal ion injection (OTOF). OTOF mass analyzers offer a high acquisition rate of mass spectra combined with a high mass resolution. The acquisition rate is between 1 kHz and 20 kHz, typically around 10 kHz. A high mass resolution of more than 10 000, up to 100 000 or even more, typically around 30 000 to 50 000, can be achieved, in particular in the mass range of digest peptides ions generated with an electrospray source.

The mass filter is preferably an RF quadrupole mass filter. The RF quadrupole rod mass filter can be switched to the mass of the ion species to be measured next in such a way that the transmission through the mass filter first is closed, then tuned to the next mass, and then opened again at the correct time of the next ion species to be measured. The RF quadrupole mass filter is preferably switched to the mass of the ion species to be measured next in such a way that the next mass is lower than the mass of the preceding ion species. The ion mobility scan can be interrupted or accelerated during the switching time of the RF quadrupole mass filter.

The fragmentation cell is preferably a flow-through cell in which the ions are not trapped. The ions are preferably fragmented by collision induced dissociation in a gas-filled cell, but can also be fragmented by electron impact or photon induced dissociation (either by using infrared or ultraviolet light sources).

A third embodiment of a method of the invention is not necessarily based on a TIMS ion mobility separator. The method provides a multi-cycle method to acquire fragment ion spectra of substances in complex substance mixtures by a mass spectrometer with an ion source, an ion mobility separator, a mass filter, an ion fragmentation cell, and a mass analyzer. In a first measurement cycle, a map with ion mobility scan times versus ion masses is measured, from which several sets of temporally separated ion species with distinct masses and distinct mobility scan times can be selected. In further measurement cycles, the ion species of a set each are selected by their mobility scan time, filtered by mass in the mass filter, and fragmented in the fragmentation cell. The fragment ion mass spectra are measured by the mass analyzer. The method is characterized by the fact that for at least one ion species, two or more fragment ion spectra are measured in different measurement cycles to improve the quality of the fragment ion spectra or a sum spectrum thereof or to verify a subsequently acquired fragment ion spectrum.

For this third embodiment, the ion mobility separator can be one of trapping ion mobility spectrometer, drift tube ion mobility spectrometer and traveling wave ion mobility spectrometer. The mass analyzer is preferably a time-of-flight analyzer with orthogonal ion injection (OTOF). OTOF mass analyzers offer a high acquisition rate of mass spectra combined with a high mass resolution. The mass filter is preferably an RF quadrupole mass filter. The fragmentation cell is preferably a flow-through cell in which the ions are not trapped. The ions are preferably fragmented by collision induced dissociation in a gas-filled cell, but can also be fragmented by electron impact or photon induced dissociation (either by using infrared or ultraviolet light sources).

In this third embodiment, the measurement of the second and further fragment ion spectrum of the at least one ion species may start after a fragment ion spectrum has been acquired for each ion species detectable in the measured map or for each ion species of a list selected from the map.

In this third embodiment, the repeated measurement of the fragment ion spectra of an ion species may end when a predetermined number of fragment ion spectra are acquired for this ion species, when a predefined quality of the fragment ion spectra or the sum spectrum thereof is obtained, when a chromatographic peak is completely scanned, or when the ion species is identified in a database search using the fragment ion spectra.

In all of these embodiments, additional mass-mobility maps may be measured, when a predetermined time interval is over, when a predetermined number of fragment ion spectra are acquired or when the present mass-mobility map essentially no longer offers sufficient unmeasured or unidentified ion species. The additional mass-mobility maps can be summed in order to increase the number of detectable ion species in the sum of the maps.

DETAILED DESCRIPTION

Figure 1:
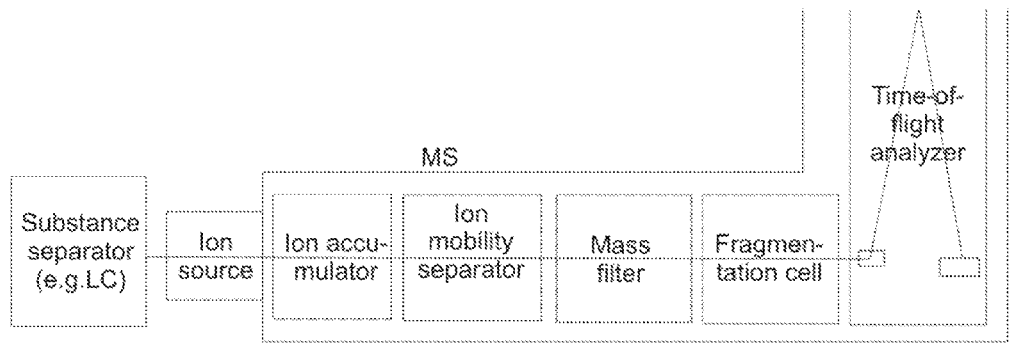
FIG. 1 shows a schematic overview of an LC-IMS-MS-MS mass spectrometer according to the state of the art. In document U.S. Pat. No. 6,960,761 B2 cited above, (D. E. Clemmer, 2001), an ion trap is used as ion accumulator, together with a drift tube ion mobility separator.
Figure 2:
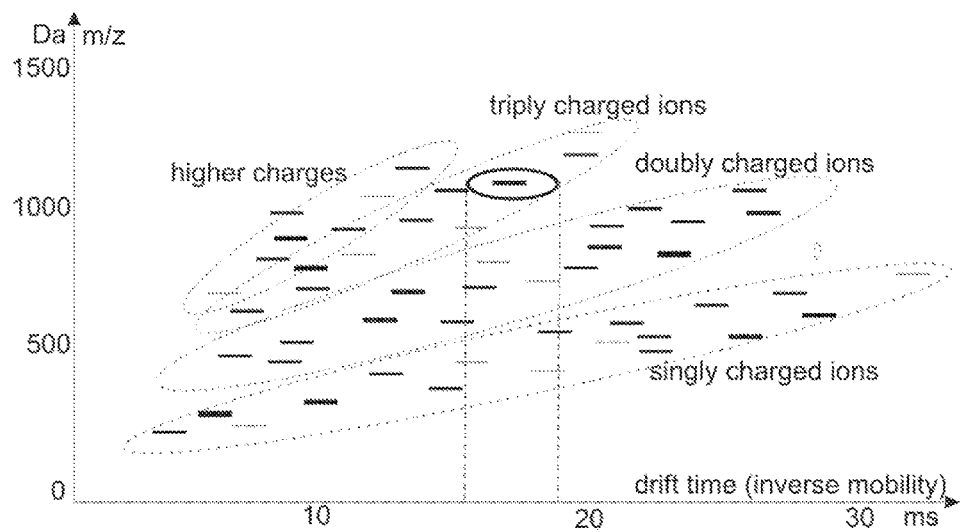
FIG. 2 shows a state-of-the-art mass-mobility map measured in a first measurement cycle of about 30 milliseconds duration with the instrument shown in FIG. 1 with a single selected ion species. For this map, only the ion mobility separator and the time-of-flight analyzer are used, without filtering masses by the mass filter and without fragmenting ions in the fragmentation cell. The map shows, as usual, the ion mass versus drift time in the drift tube. A single ion species is selected for further measurements in a subsequent measurement cycle.
Figure 3:
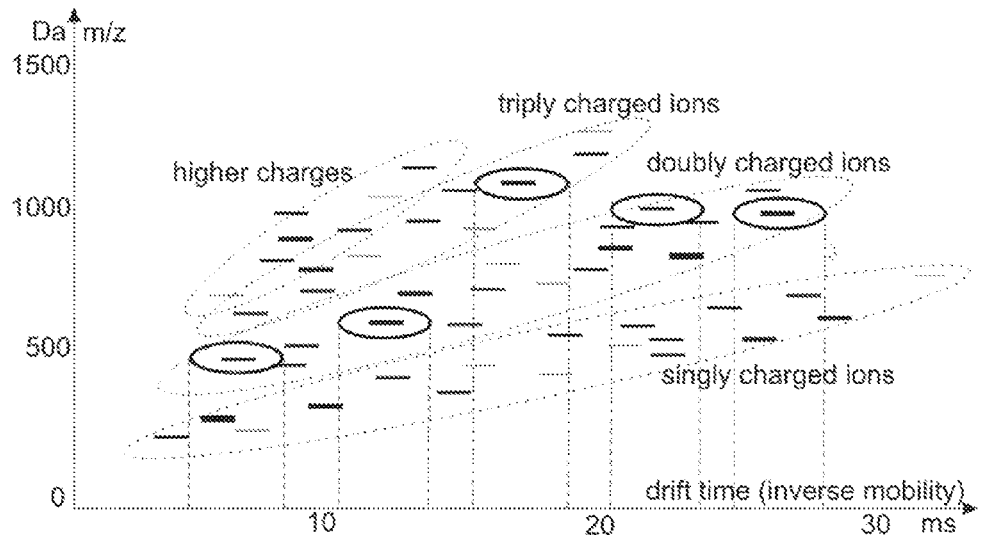
FIG. 3 presents a state-of-the-art mass-mobility map measured according to the invention by D. E. Clemmer with selection of five ion species of interest, as indicated by the ellipses. Thereafter, five fragment ion mass spectra of the five selected ion species can be measured in a single measurement cycle. The ion species are selected in such a manner, that a switching of the voltages for the mass filter can be performed between the drift times of the different ion species selected.
Figure 4:
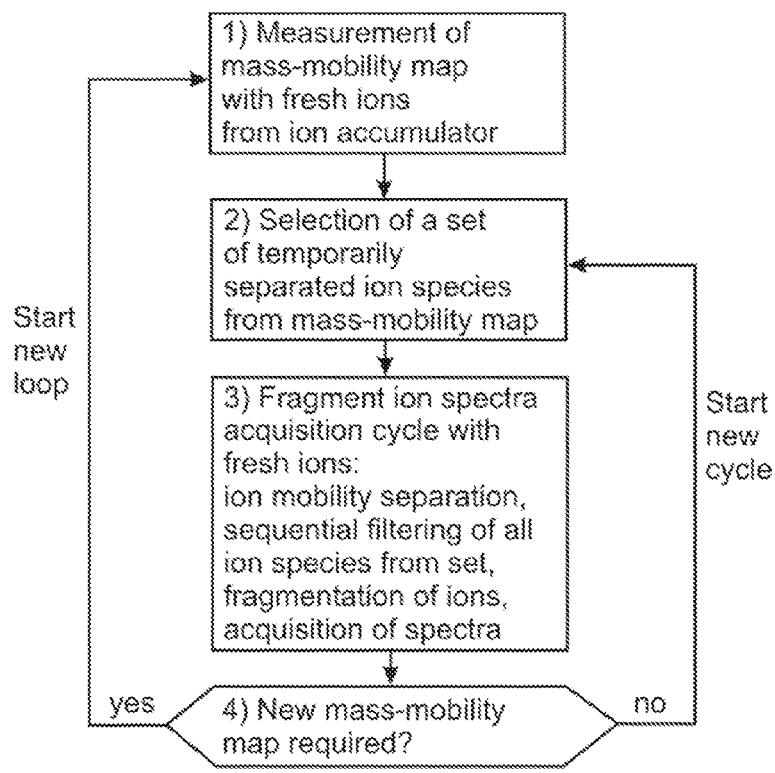
FIG. 4 presents the essential steps of a multi-cycle method for the measurement of numerous fragment ion mass spectra as a flow chart. The diagram introduces the terms "loop" and "cycle". (1) In a first measurement with fresh ions from the accumulator, starting a new loop, a mass-mobility map is measured. (2) From this map, ion species of interest are selected. In state-of-the-art methods, about five ion species were selected, as demonstrated in FIG. 3. (3) In a measurement cycle of the same duration as for the map measurement, fresh ions from the accumulator are again separated in time by their mobility, but the ions of interest are now selected one after the other by the mass filter, fragmented in the fragmentation cell, and the fragment ion mass spectra are acquired by the time-of-flight mass analyzer. (4) If no new mass-mobility map is required, more ions species may be selected from the same mass-mobility map, and the corresponding fragment ion mass spectra may be obtained in a new measurement cycle. Otherwise, a new mass-mobility map may be measured, starting a new loop. The measurement loops with fresh mass-mobility maps may be repeated in time intervals of 0.5 to three seconds, depending on the time behavior of the substance separation device. In state-of-the-art methods of this type, about 30 intermediate measurement cycles per second may be performed, resulting in a capacity of about 150 fragment ion spectra per second.

The expressions "separator" and "separation" are used herein for devices and methods which separate different substances or different ion species in time. Chromatography, capillary electrophoresis, and ion mobility spectrometry are separation methods. The term "filter" is applied to devices and methods which let pass only selected ion species from a larger variety offered. An example is the RF quadrupole mass filter, capable of filtering ions by mass.

A "fragment ion mass spectrum measurement cycle", in short "cycle" or "measurement cycle", starts with the transfer of fresh ions from the accumulation unit to the ion mobility scan unit, and measures a set of fragment ion mass spectra from ion species, selected from a mass-mobility map. A "measurement loop" is a term used herein having a special meaning, and starts with the measurement of a new mass-mobility map, followed by several fragment ion mass spectrum measurement cycles.

The "mobility scan time" or "mobility scan duration" is defined as the duration of an ion mobility scan over an interesting range of ion mobilities, usually the range of the mobilities of the ions stored.

The invention provides methods for acquiring fragment ion spectra of substances in a sample. In a first measurement cycle, ions of the substances are temporally separated by an ion mobility separator and then analyzed in a mass analyzer without fragmentation to provide a map of ion species with ion mobility scan times versus ion masses. Multiple sets of ion species are selected from the map, each set comprising ion species which are separated from each other according to ion mobility scan time. In each of the following measurement cycles, ion species of the substances are temporally separated by the ion mobility separator and the mass filter is temporally adjusted to the mass of ion species of one of the sets during the ion mobility scan time of the selected ion species, the filtered ion species are fragmented and fragment ion spectra are acquired in the mass analyzer. The invention is characterized in that ions are separated by a trapping ion mobility spectrometer (TIMS).

A second mass-mobility map can be measured and second sets of ion species can be selected from the second map when a predetermined time interval is over, when a predetermined number of fragment ion spectra are acquired or when fragment ion spectra of substantially all ion species of the first map are acquired. Ions can be accumulated prior to measuring the first and second map. The duration of accumulation of the second map can, for example, be increased compared to the first map and the second sets substantially comprise ion species which are not selected from the first map. The ion mobility ranges of the first and the second map as well as the ion mobility scan times of the measurement cycles following the measurement of the first and second map can be different. Furthermore, fragment ion spectra of at least one ion species can be measured in subsequent measurement cycles and added together to improve quality.

The mass spectrometer with up-front substance separator and with ion mobility separator as shown in FIG. 1 is mainly used for the identification of high numbers of peptides and proteins by their fragment ion mass spectra. The invention proposes to use a trapped ion mobility spectrometer ("TIMS"), resulting in a mass spectrometer as presented in FIG. 5. The introduction and use of TIMS instead of a drift tube mobility spectrometer is not just a simple replacement of a long instrument by a much shorter one; the embodiments offer several advantages, some of which become only visible with a deep knowledge of the characteristics of TIMS. In addition to the embodiment which just introduces TIMS instead of the prior-art mobility separator, a preferred embodiment uses TIMS with parallel ion accumulation.

The present invention is mainly based upon a trapped ion mobility spectrometer "TIMS" such as described in document U.S. Pat. No. 7,838,826 B1 (M. A. Park, 2008), preferably additionally equipped with an extra up-front accumulation unit capable of accumulating the ions generated during the scan phases of the mobility spectrometer and transferring the stored ions in a short time of about a millisecond into the ion mobility spectrometer. A particularly favorable embodiment therefore comprises DC generators which deliver additional DC voltages to generate a spatial zoom.

Notably, TIMS is the only type of ion mobility spectrometer that shows an increasing ion mobility resolution with longer ion mobility scan durations.

The number of ions collected by any up-front ion collection unit, such as an ion trap, and the transfer to the ion mobility separator is greatly limited by the effect of repelling Coulomb forces between the accumulated ions, in short called "space charge effect". To overcome problems with space charge, preferred embodiments of the invention use the TIMS device with parallel accumulation, allowing for the collection of more ions than with usual ion accumulators because the ions are already accumulated, separated by their ion mobility and less influenced by space charge. As long as the accumulation periods are not excessively long, this device uses almost all ions delivered by the ion source for measurements, i.e., these modes show highest sensitivity and highest ion utility rates.

Figure 5:
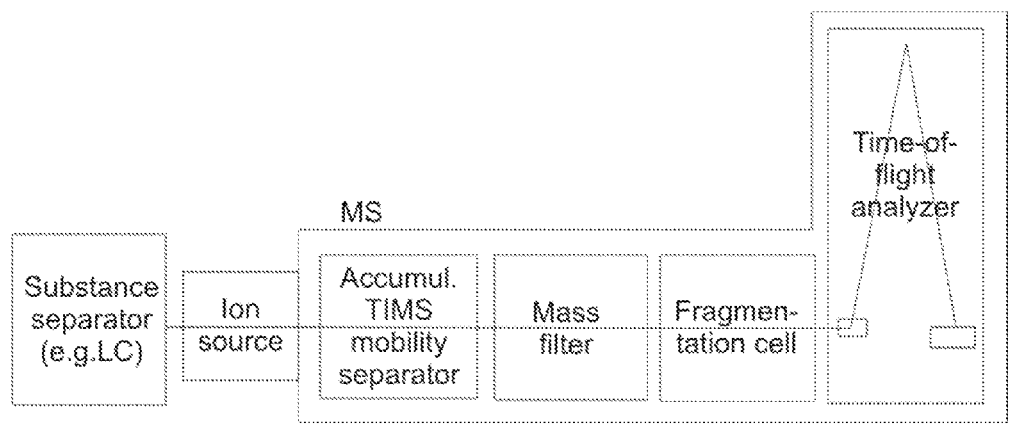
FIG. 5 illustrates a mass spectrometer used for the methods according to this invention, replacing the conventional combination of ion accumulator and ion mobility separator by a trapped ion mobility separator (TIMS) with parallel ion accumulation. This replacement gives rise to a number of partially surprising advantages, mainly with respect to the detectability and identification of peptide ions.
Figure 6:
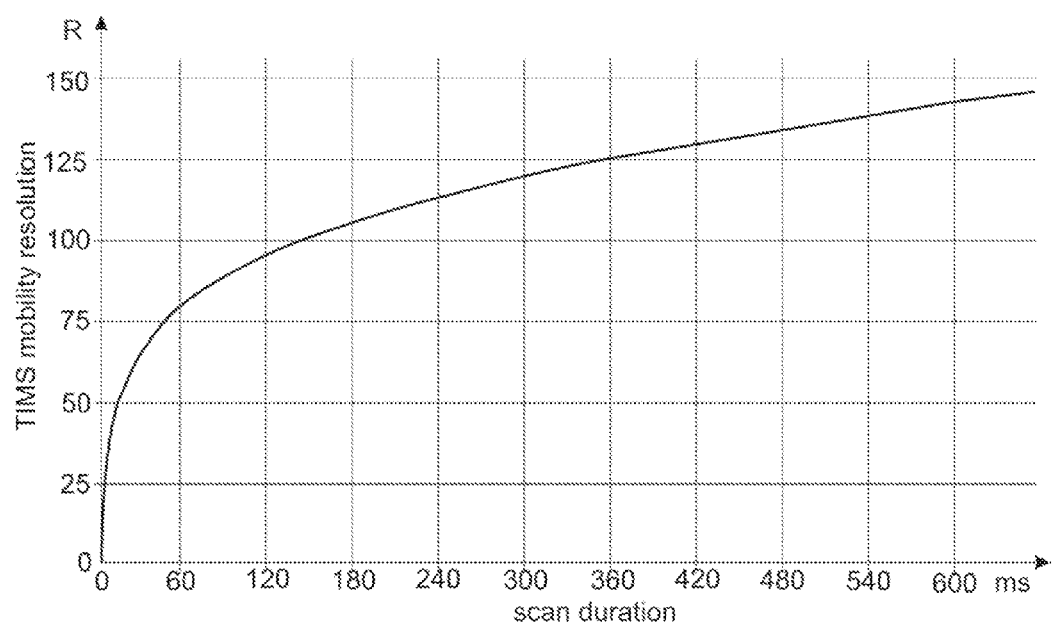
In FIG. 6, the ion mobility resolution of the TIMS instrument is plotted as function of the duration needed for a scan over the full range of ion mobilities. With a scan duration of only 20 milliseconds, a mobility resolution of about $R_{mob}$=60 is achieved for an ion mobility of $K_o$=0.5, while with 300 milliseconds scan duration, the resolution rises to $R_{mob}$=120.

It has been shown by experiments with instruments illustrated in FIG. 5 that the time needed to measure a fragment ion mass spectrum, with switching the quadrupole filter to the new mass, letting pass the selected ion species, fragmenting the ions of this species, and acquiring the fragment ion mass spectrum by the time-of-flight analyzer, amounts to about 2.5 milliseconds only. Furthermore, a time of about 1.5 milliseconds is needed for the transfer of ions from the accumulator to the ion mobility scanning unit, and to damp the ion movements within the gas flow at their new location. A measurement procedure operating with 20 milliseconds ion mobility scan duration and 1.5 milliseconds transfer time, i.e. with 21.5 milliseconds per cycle, results in one mass-mobility map and about 45 measurement cycles per second with possible measurements of eight fragment ion mass spectra each. Thus the measurement capacity amounts to 45×8=360 fragment ion spectra per second, outperforming any state-of-the-art mobility separator.

This capacity of 360 fragment ion mass spectra per second for the basic operation mode is an approximation only, strongly dependent on the time needed for a single measurement of a fragment ion mass spectrum. If this time, assumed to be 2.5 milliseconds, can be shortened to 2.0 milliseconds, the capacity increases to about 450 fragment ion spectra per second. The true capacity may amount to a number between 300 and 450 fragment ion mass spectra per second. In experiments, a capacity of 380 fragment ion mass spectra per second was revealed.

A fragment ion mass spectrum usually is added from about 25 single spectrum acquisitions of the time-of-flight analyzer, if operated at 10 kilosamples per second, to improve the quality of the spectrum.

Figure 9:
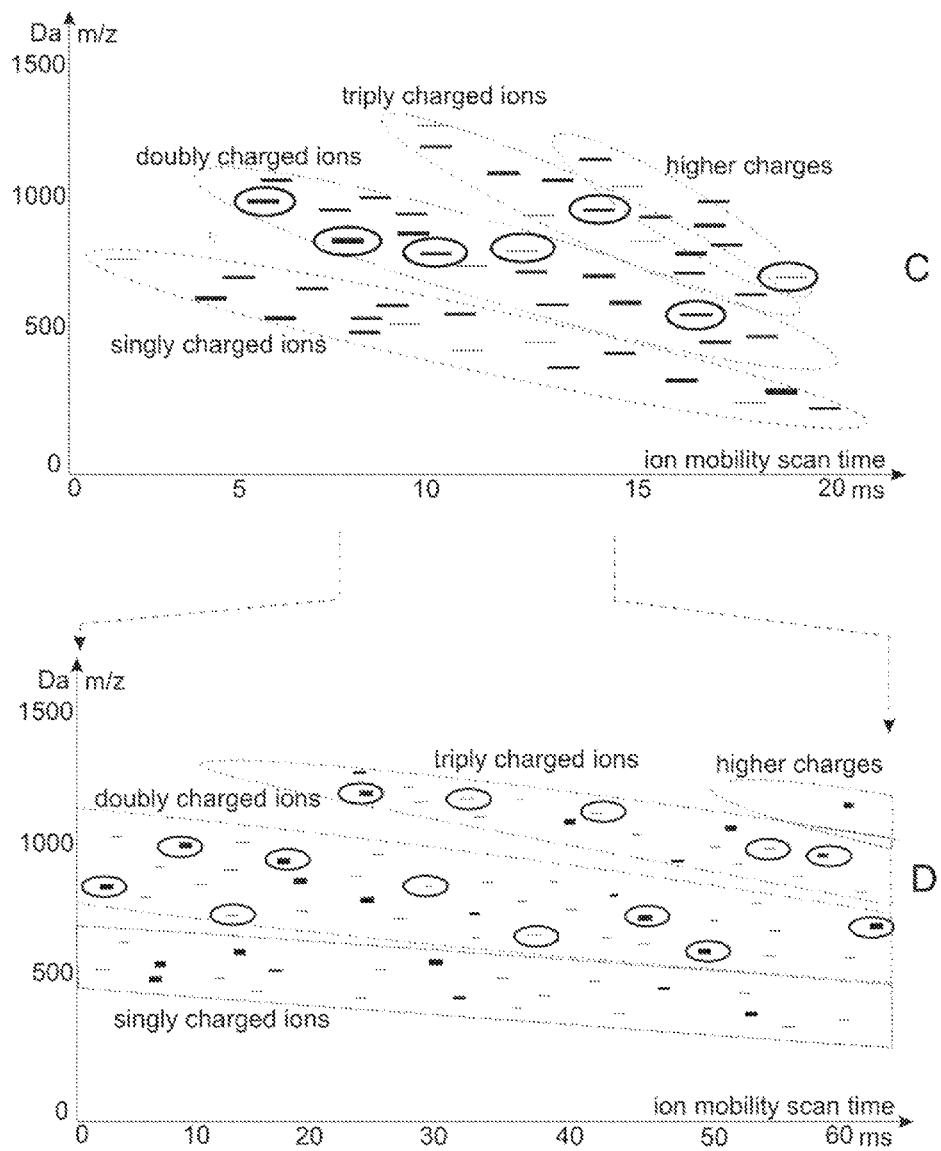
FIG. 9 presents in the upper part (C) an artificially constructed mass-mobility map showing the whole range of mobilities, and in the lower part (D) a mass-mobility map with higher ion mobility resolution restricted to about ⅓ by application of a spatial zoom. Such maps can be measured using the TIMS mobility separator and the time-of-flight analyzer of the mass spectrometer of FIG. 5, equipped with a voltage generator for the additional voltages needed for the spatial zoom. In the upper part (C) it is demonstrated that about eight selected ion species can be measured in each measuring run of 20 milliseconds duration (in the figure, seven ion species are selected), resulting in a capacity to measure more than 300 fragment ion mass spectra per second. The ion mobility range of the mass-mobility map (D) in the lower part represents only ⅓ of the full mobility range by applying correctly selected voltages to the ends of the flat ion accumulation or ion mobility scanning regions. By a three times longer accumulation of 60 milliseconds three times more ions are collected, and by a nine times slower scan (corresponding to 180 milliseconds for the total mobility range), a mobility resolution $R_{mob} \geq 100$ is achieved, both increasing detectability. Considerably more ion species can be detected in the corresponding mass-mobility map; the exact improvement depends on the mixture of substances. Within a single measurement cycle, about 24 ion species may be selected; in the figure, only 14 ion species are marked. Up to 350 ion fragment mass spectra may be acquired in a single second, and the probability of obtaining a high number of useful fragment mass spectra is considerably increased. Again, some of the measurement cycles may be used to repeatedly measure the same ion species in order to improve the spectrum quality.

As stated above, a basic measurement procedure with TIMS already allows for more than 300 fragmentation ion spectra per second. TIMS features a relatively high ion mobility resolution in the order of $R_{mob}$=60 for short ion mobility separation times of 20 milliseconds only. Compared with the state of the art, the basic mode of operation already constitutes a strong improvement, with more fragment ion spectra per second and higher ion mobility resolution. As an example, FIG. 9 presents in the upper part (C) an artificially created mass-mobility map showing the whole range of mobilities of ion species in a sample with a selection of seven ion species per cycle. Such a map can be measured using the TIMS as mobility separator and the time-of-flight analyzer of the mass spectrometer of FIG. 5. From this upper part (C) it may be taken that up to eight selected ion species can be measured in each measuring cycle of 21.5 milliseconds duration, resulting in the measurement capacity of more than 300 fragment ion mass spectra per second.

This mode with short ion mobility scan durations and high numbers of measurement cycles per second is particularly suited to accurately quantify selected proteins or peptides in complex mixtures with high precision. There are quantifications methods known using labeling peptides of interest with isobaric mass tags via cleavable linkers. Especially tagged peptide ions then separate "reporter ions" in the collision cell which may be measured in each measurement cycle covering a complete LC peak to improve the accuracy of the quantitation. This method may not need a high detectability to get high numbers of ion species, the selection of a few tagged precursor ions may suffice the analytical requirements. This IMS-MS-MS based method of quantitation is of particular interest for the measurement of relative abundances of substances with high accuracy.

On the other hand, the analytical goal may be directed to identify as many substances as possible. Even high-performance ion sources usually do not deliver several hundreds of ion species which are detectable in a map measured at an accumulation duration of only 20 milliseconds. Thus the capacity of more than 300 fragment ion mass spectra per second cannot be fully exploited in this case.

The detectability of ion species in the mass-mobility map is one of the main problems of this multi-cycle method. If an ion species cannot be detected, no fragment ion spectrum can be obtained from this ion species in a data dependent approach. Higher detectability requires higher amounts of ions to be accumulated. For an optimized ion source, higher amounts of ions can only be obtained by enlarging the accumulation duration.

For state-of-the-art methods, the number of fragment ion mass spectrum acquisition cycles per unit of time will be greatly reduced by enlarged accumulation durations because the prolonged time cannot be used to increase the number of measuring cycles.

TIMS with parallel ion accumulation provides the unique possibility to use longer accumulation durations with the advantage that the correspondingly slower ion mobility scan increases the ion mobility resolution. With longer accumulation and ion mobility scan durations, the number of accumulated ions increases and the mobility resolution is improved, resulting in a better detectability because the signal-to-noise is increased by sharpening the ion mobility peaks. At the same time, the sensitivity increases and more ion species can be detected in the mass-mobility map. If the accumulation duration is increased to 100 milliseconds, and one mass-mobility map is measured per second, nine measurement cycles with about 40 fragment ion mass spectra each can be performed with five times more ions in the mass-mobility map. Interestingly, if the fragment ion mass spectrum acquisition time is again assumed to be exactly 2.5 milliseconds, the measurement capacity results in about 9×40=360 fragment ion spectra per second, remaining almost constant. Five times more ions per cycle increases the number of detectable ion species in the mass-mobility map considerably; the exact improvement depending on the mixture of substances. It is, however, justifiable to assume that the number of detectable ions species increases by at least a factor of two.

Figure 7:
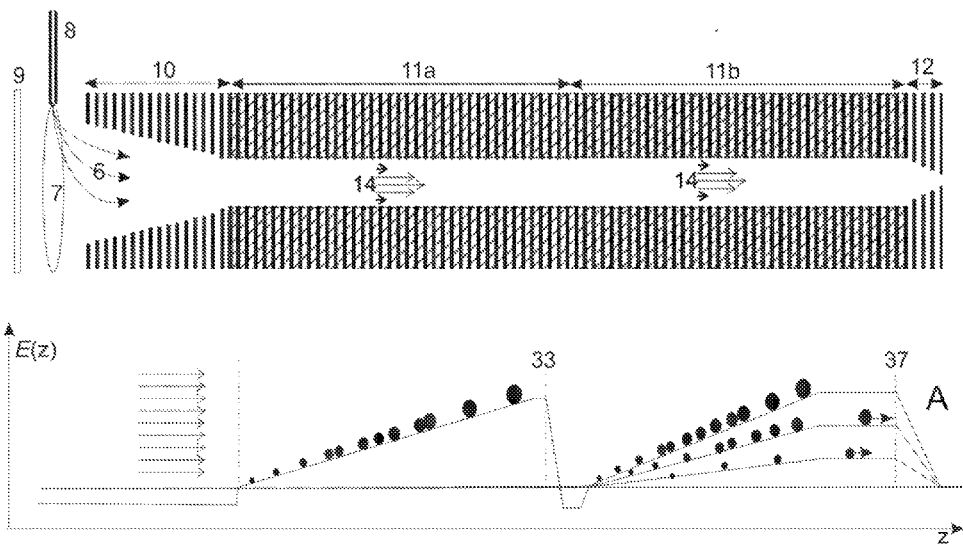
FIG. 7 schematically depicts an embodiment of the mobility spectrometer presented in patent application U.S. Ser. No. 14/614,456 ("Trapping Ion Mobility Spectrometer with Parallel Accumulation", M. A. Park and M. Schubert). Ions are introduced through entrance capillary (8) entrained by gas (7) into the first vacuum stage of the mass spectrometer. The entrained ions (6) are pushed by repeller (9) through an RF ion funnel (10) into the trapping ion mobility spectrometer (11a, 11b). The trapping ion mobility spectrometer comprises an elongated tunnel (11), divided into an ion accumulation unit (11a) and an ion mobility scan unit (11b). A gas flow (14) drives the ions through the elongated tunnel (11). The spectrometer furthermore comprises an RF voltage supply unit (not shown) for RF voltages at quadrants of the tunnel electrodes and DC voltage supply units (likewise not shown) for the generation of the electric field barrier in an axial direction within the two tunnel units, contacting the electrodes at locations (33) and (37). A quadrupolar RF field inside the tunnel (11) holds the ions near to the axis of the device. Chains of resistors between the diaphragms in both tunnel units produce the two electric DC field barriers for the ion accumulation unit (11a) and for the ion mobility scan unit (11b), shown in diagram (A) in the lower part of the figure. The gas flow (14) drives the ions against the electric field barriers, separating the ions by their ion mobility. During the ion mobility scan, the voltage applied to electrode (37) of the scan unit (11b) is steadily decreased, thereby releasing ion species with increasing mobility, resulting in an ion mobility spectrum.

TIMS with parallel accumulation is illustrated in some detail in FIG. 7, operated with the electric field barrier shown in diagram (A). A detailed description of a system of this type can be found in patent application U.S. Ser. No. 14/614,456 ("Trapping Ion Mobility Spectrometer with Parallel Accumulation", M. A. Park and M. Schubert). Ions are introduced through entrance capillary (8) entrained by gas (7) into the first vacuum stage of the mass spectrometer. The entrained ions (6) are pushed by repeller (9) through the RF ion funnel (10) into the ion mobility spectrometer (11a+11b). A gas flow (14) drives the ions through the mobility spectrometer (11a+11b). The spectrometer comprises an elongated tunnel (11a+11b), divided into an ion accumulation unit (11a) and an ion mobility scan unit (11b), an RF voltage supply unit (not shown) for RF voltages at quadrants of the tunnel electrodes and DC voltage supply units (likewise not shown) for the generation of the electric field profiles in axial direction within the two tunnel units, contacting the electrodes at locations (33) and (37). A quadrupolar RF field inside the tunnels keeps the ions near to the axis of the device. Chains of resistors between the diaphragms in both tunnel units produce the two field barriers for the ion accumulation unit (11a) and the ion mobility scan unit (11b), shown in diagram (A) below. The gas flow (14) drives the ions against the electric field barriers, separating the ions by their ion mobility. These electric field barriers allow for a normal operation without spatial zoom. In comparison with usual ion accumulation devices, the accumulation time can be prolonged without space charge damages. However, if too long accumulation (and scan) periods are applied, even in this device the ions collected on the field ramps may become overcrowded.

Therefore, even here the elongation of accumulation and scan durations is limited. The longest useful accumulation duration is reached when the further collection of ions is again impaired by space charge effects.

Figure 8:
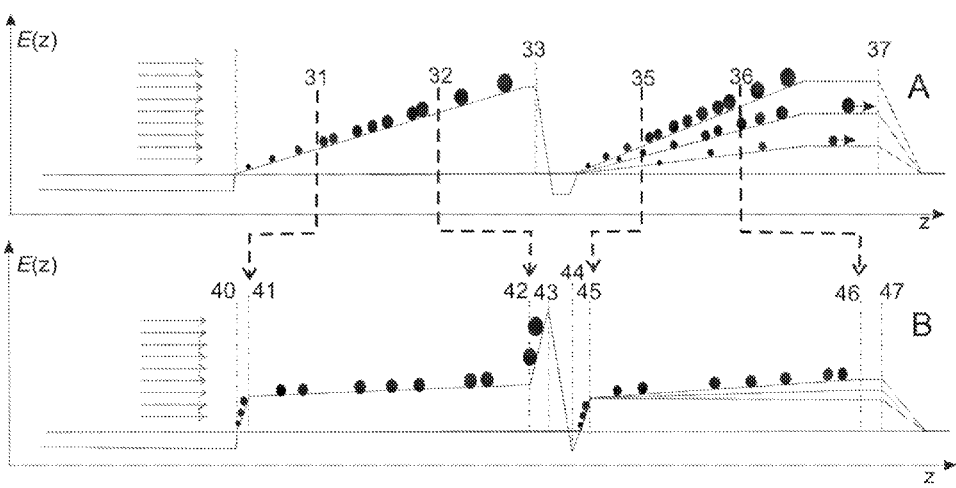
FIG. 8 illustrates the operation of a spatial zoom mode preferably used for this invention, presenting an electric field barrier (A) of the usual operation without spatial zoom, and a barrier (B) of the zoomed operation. The spatial zoom is based upon field barrier (B) exhibiting a wide and flat electric field gradient positioned between z-locations (41) and (42) and a field peak with steep field gradient between (42) and (43), keeping back ions of low mobility during ion accumulation. Ions of an interesting range of ion mobilities between locations (31) and (32) of the non-zoomed barrier (A) are accumulated on the flat part of the field barrier between (41) and (42). The ions are spatially decompressed to reduce the effects of space charge, allowing for the undisturbed collection of many more ions using longer accumulation duration. The ion mobility scan unit (11b) shows a similar electric field profile, however without the field peak. Once the ions stored between (45) and (46) are scanned according to their ion mobility, the ions of the accumulation unit are transferred, in about a millisecond, to the ion mobility scan unit (11b), thereby letting pass the non-interesting ions of low mobility stored at the ramp of the peak between locations (42) and (43). The ion species stored between locations (45) and (46) can be scanned much slower than usual, resulting in a high ion mobility resolution.

If the accumulation of ions is impaired by space charge, a "spatial zoom mode" further offers an improved mode of operation. In case of overcrowding the accumulator with ions, the spatial zoom mode should be used. The spatial zoom is a particularly favorable mode of operation based upon field barrier (B) of FIG. 8 exhibiting a wide and flat electric field gradient positioned between z-locations (41) and (42) and a field peak with steep field gradient between (42) and (43), keeping back ions of low mobility during ion accumulation. Ions of an interesting range of ion mobilities, for instance between locations (31) and (32) of the non-zoomed profile (A), are accumulated on the flat part of the field barrier between (41) and (42). The ions are spatially decompressed to reduce the effects of space charge, allowing for the collection of many more ions using longer accumulation times. The ion mobility scanning unit (11*b*) shows a similar electric field barrier, however, without the field peak. Once the ions stored between (45) and (46) are scanned according to their ion mobility, the ions of the accumulation unit are transferred, in about a millisecond by switching off the voltage at locations (41-43), to the ion mobility scanning unit, thereby letting pass the non-interesting ions of low mobility stored at the ramp of the field peak. The ions collected between locations (45) and (46) then can be scanned with very low scanning speed and correspondingly high ion mobility resolution.

As an example for the application of the spatial zoom mode, the ion mobility range of the mass-mobility map (D) in the lower part of FIG. 9 represents only ⅓ of the full mobility range by applying correctly selected voltages to the ends of the flat ion accumulation or ion mobility scanning regions. By a three times longer accumulation of 60 milliseconds about three times more ions are collected, and by a nine times slower scan speed (corresponding to a full scan duration of 180 milliseconds for the total mobility range), a mobility resolution $R_{mob} \geq 100$ is achieved. Considerably more ion species can be selected for a single measuring cycle. Thus more ion species can be detected, selected and identified in a single measurement cycle by this procedure. The capacity with more than 300 ion fragment mass spectra is not enlarged, but by the strongly increased detectability, many more fragment ion mass spectra can be measured of precursor ions which cannot be detected in state-of-the-art measuring devices and modes, not even in the other operation modes of TIMS.

The range of ion mobilities of the spatial zoom mode may be altered from one loop to the next loop. Subsequent loops may cyclically use different ranges of ion mobilities. The time between the measurement loops may vary between half a second and several seconds, depending on the speed with which the mixture of substances delivered by the up-front substance separator changes its composition. During an LC run, the mixture of substances changes continuously in composition, varying the molecular weights, in the average, from low-mass substances to substances of higher mass. Therefore, also the average ion mobility will vary along the LC run. This variation may be considered by the selection of the ion mobility ranges for the spatial zoom mode.

A part of the still unused measurement capacity may be used to measure the fragment ion mass spectra of low abundance ion species over and over to improve their quality by adding the spectra together. The number of repetitions of spectrum acquisition in subsequent measurement cycles may be calculated from the abundance, or may be determined by the increasing quality of the resulting fragment spectrum. The quality of peptide fragment ion spectra may, for instance, be determined by the number of mass differences in the spectrum which exactly correspond to masses of amino acids, or by the quality of the protein identification from the summed fragment ion mass spectrum. Repetitive acquisitions may even be continued in a new loop after the acquisition of a new mass-mobility map; a list of ion species to be measured repeatedly may be maintained and updated within the computer of the mass spectrometer. Additionally, an exclusion list may be maintained holding the successfully identified ion species to avoid repetitive measurements of these ion species; especially when a separation unit for substances, e.g. a liquid chromatograph, is used with the mass spectrometer.

An example of an operation method using the spatial zoom may comprise the following steps. At first, a range of ion mobilities for the measurements of fragment ion mass spectra has to be chosen, and the corresponding mass-mobility map has to be measured for a new loop of measurements. A zoomed mass-mobility map is presented in the lower part D of FIG. 9, zooming (in this example) about ⅓ of the full mobility range, and collecting the ions and scanning mobilities for about 60 milliseconds. With this type of spatial zoom, and with 2.5 milliseconds for the acquisition of a fragment ion mass spectrum, up to 24 ions of interest may be selected from this mass-mobility map. (In FIG. 9, only 14 ion species are selected). The ions must be sufficiently separated in time by their different mobilities to enable high quality switching of the mass separator. The time between the selected ions has to be chosen such that the RF quadrupole ion mass filter can be switched electronically to the next mass to be selected. A high quality power supply for a good quadrupole mass filter, particularly developed for this purpose, may need about 600 nanoseconds for a switch, leaving a time of about 1.9 milliseconds for mass filtering. Favorably, the switching of the voltages at the mass filter has to be performed in such a way that at first the filter is closed (by slightly increasing the DC voltage), then the voltages are changed and the filter is opened again for the selected ion species. At the end of mass filtering for this ion species, the filter again is closed and switched to the next ion species. In this manner, the mass filter not only can filter the mass of a specific ion species, but also correctly select the right time interval for this ion species.

The invention claimed is:

1. A multi-cycle method to acquire fragment ion spectra of substances in complex substance mixtures by a mass spectrometer with an ion source, an ion mobility separator, a mass filter, an ion fragmentation cell, and a mass analyzer, wherein in a first measurement cycle a map of ion species with ion mobility scan times versus ion masses is measured, from which several sets of temporally separated ion species with distinct masses and distinct mobility scan times can be selected, and wherein in further measurement cycles the ion species of a set each are selected by their mobility scan time, filtered by mass in the mass filter, and fragmented in the fragmentation cell, and wherein the fragment ion mass spectra are measured by the mass analyzer, characterized by the fact that a trapped ion mobility spectrometer (TIMS) is used as ion mobility separator, wherein the separator is operated in a parallel accumulation mode in which ions are provided from the ion source to the separator during a measurement cycle in an accumulator unit of the separator at a rising edge of an electric field barrier such that the ions are spatially separated by their ion mobility along the rising edge.

2. The multi-cycle method according to claim 1, wherein the ion accumulation durations of the separator are adapted to obtain a predetermined number of detectable ion species in the map.

3. The multi-cycle method according to claim 2, wherein the ion mobility scan durations substantially equal the ion accumulation durations.

4. The multi-cycle method according to claim 2, wherein a spatial zoom mode is applied to enlarge the number of detectable ion species and to increase the ion mobility resolution by choosing selected ranges of ion mobility.

5. The multi-cycle method according to claim 4, wherein the ion mobility ranges of the spatial zoom are adapted to the ion mobility distribution of the ion species generated from the substance mixture.

6. The multi-cycle method according to claim 1, wherein the fragment ion mass spectra of selected ion species are measured repeatedly in subsequent measurement cycles to improve their spectrum quality.

7. The multi-cycle method according to claim 6, wherein the repetitive measurement of further fragment ion mass spectra of the same ion species is ended when a predefined quality is obtained or when the ion species is identified in a database search using the fragment ion spectra.

8. The multi-cycle method according to claim 6, wherein an up-front chromatograph is used to separate substances, and wherein the repetitive measurements of fragment ion mass spectra of the same selected ion species is continued to measure the ion species over a full peak of the chromatogram for accurate quantification of selected substances.

9. The multi-cycle method according to claim 8, wherein the selected ion species is a reporter ion split from a substance chemically labeled with a mass tag.

10. The multi-cycle method according to claim 1, wherein a second mass-mobility map for a second measurement loop is measured when a predetermined time interval is over, when a predetermined number of fragment ion spectra is acquired or when the present mass-mobility map essentially does no longer offer sufficient unmeasured ion species to be selected.

11. The multi-cycle method according to claim 10, wherein the mobility range of the second mass-mobility map differs from the mobility range of the first mass-mobility map.

12. The multi-cycle method according to claim 10, wherein the ion accumulation duration of the second mass-mobility map differs from the ion accumulation duration of the first mass-mobility map.

13. The multi-cycle method according to claim 12, wherein the ion accumulation duration of the second mass-mobility map is increased compared to the ion accumulation duration of the first mass-mobility map in order to obtain more detectable ion species.

14. The multi-cycle method according to claim 1, operating on substance mixtures delivered from an up-front substance separator, such as a liquid chromatograph or a capillary electrophoresis unit.

15. The multi-cycle method according to claim 1, wherein a time-of-flight mass analyzer with orthogonal ion injection (OTOF) is used as mass analyzer.

16. The multi-cycle method according to claim 1, wherein the mass filter comprises an RF quadrupole mass filter.

17. The multi-cycle method according to claim 16, wherein the ion mobility scan is interrupted during the switching time of the RF quadrupole mass filter.

18. The multi-cycle method according to claim 1, wherein two or more fragment ion spectra are measured for at least one ion species in different measurement cycles and added together to improve the quality of the fragment ion spectra or a sum spectrum thereof.

19. The multi-cycle method according to claim 18, wherein the measurement of the fragment ion mass spectra of the at least one ion species is ended when a predefined quality of the spectrum is obtained or when the selected ion species is identified in a database search using the fragment ion spectra.

20. The multi-cycle method according to claim 1, wherein the selected ion species is a reporter ion split from a substance chemically labeled with a mass tag.

21. The multi-cycle method according to claim 16, wherein the RF quadrupole mass filter is switched to the mass of the ion species to be measured next in such a way that the transmission through the mass filter first is closed, then tuned to the next mass, and then opened again.

22. The multi-cycle method according to claim 16, wherein the quadrupole mass filter is switched from the mass of a preceding ion species to the next ion species of a set in such a way that the mass of the next ion species is lower than the mass of the preceding ion species.

23. The multi-cycle method according to claim 15, wherein the time needed for acquiring the fragment ion spectrum of one of the selected ion species is approximately 2.5 milliseconds or less.

* * * * *